United States Patent [19]

Boar et al.

[11] Patent Number: 5,665,747

[45] Date of Patent: Sep. 9, 1997

[54] 1,1-BIS(HETEROAZOLYL)ALKANE DERIVATIVES AND THEIR USE AS NEUROPROTECTIVE AGENTS

[76] Inventors: Robin Bernard Boar, 25 Meadow Way Letchworth, Hertfordshire, Great Britain, SG6 3JB; Duncan Alastair Gray, Little Cefn Farm Hyssington Churchstoke, Powys, Great Britain, SY15 6EQ; Dennis Mark O'Shea, 26 Hurtstlings Welwyn Garden City, Hertfordshire, Great Britain, AL7 3LX

[21] Appl. No.: 485,719

[22] Filed: Jun. 7, 1995

Related U.S. Application Data

[62] Division of PCT/SE95/00604, May 29, 1995.

[30] Foreign Application Priority Data

Jun. 7, 1994 [SE] Sweden .................. 9401965

[51] Int. Cl.$^6$ .................................................. A61K 31/425
[52] U.S. Cl. ................................. 514/365; 548/203
[58] Field of Search ........................ 514/365; 548/203

[56] References Cited

U.S. PATENT DOCUMENTS 4,371,734  2/1983  Seybold ........................... 544/300

FOREIGN PATENT DOCUMENTS 2131966  3/1995  Canada .

OTHER PUBLICATIONS

Dondoni et al., "Synthesis of (Trimethylsilyl)thiazoles and Reactions with Carbonyl Compounds. Selectivity Aspects and Synthetic Utility," J. Org. Chem., vol. 53, pp.1748–1861 (1988).

Hodges et al., "Reactions of Lithiooxazole," J. Org. Chem., vol. 56, pp.449–452 (1991).

Pridgen et al., "A New Facile Synthesis of 2–Aroyloxazoles from 2–Lithiooxazoles," Synthesis, pp.1048–1050 (Dec. 1984).

Roussel et al., "Synthèse et étude spectrale infrarouge des deutéro–thiazoles," Bulletin Soc. Chim. France, pp.2075–2078 (1962).

Strekowski et al., "Efficient Preparation of Ketones from N–(Ethoxymethylene)aniline and Organometallic Reagents," J. Org. Chem., vol. 54, pp.6120–6123 (1989).

Primary Examiner—Robert Gerstl
Attorney, Agent, or Firm—White & Case

[57] ABSTRACT

The present invention relates to novel heterocyclic compounds having the general formula (1)

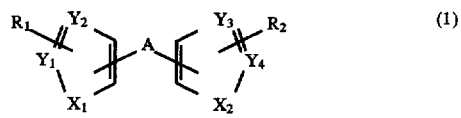

wherein:

$X_1$ and $X_2$ are independently O, S or Se;

$Y_1$ and $Y_2$ are independently C or N with the proviso that at least one of $Y_1$ and $Y_2$ is N;

$Y_3$ and $Y_4$ are independently C or N with the proviso that at least one of $Y_3$ and $Y_4$ is N;

$R_1$ and $R_2$ each represent one or more groups independently selected from H, lower alkyl, lower alkoxy-lower alkyl, hydroxy-lower alkyl, lower acyloxy-lower alkyl or $CF_3$;

and A is

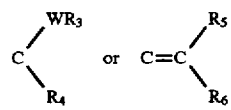

geometrical and optical isomers and racemates thereof where such isomers exist, as well as pharmaceutically acceptable acid addition salts thereof and solvates thereof; having therapeutic activity, processes and intermediates for their preparation, pharmaceutical formulations containing said compounds and the medicinal use of said compounds.

6 Claims, No Drawings

1,1-BIS(HETEROAZOLYL)ALKANE DERIVATIVES AND THEIR USE AS NEUROPROTECTIVE AGENTS

This is a divisional of International application Ser. No. PCT/SE95/00604, filed May 29, 1995.

FIELD OF THE INVENTION

The present invention relates to novel heterocyclic compounds having therapeutic activity, processes and intermediates for their preparation, pharmaceutical formulations containing said compounds and the medicinal use of said compounds.

BACKGROUND OF THE INVENTION

There exists a large group of acute and chronic neuropsychiatric disorders for which safe and clinically effective treatments are not currently available. This diverse group of disorders encompasses a broad spectrum of initial events which are characterised by the initiation of progressive processes that sooner or later lead to neuronal cell death and dysfunction. Stroke, cerebral ischaemia, trauma or a neurodegenerative disease such as Alzheimer's disease or Parkinson's disease are all commonly occurring conditions that are associated with neurodegeneration of the brain and/or spinal cord.

The ongoing search for potential treatments of neurodegenerative disorders has involved investigation of excitatory amino acid antagonists, inhibitors of lipid peroxidation, calcium channel antagonists, inhibitors of specific pathways of the arachidonic acid cascade, kappa opioid agonists, adenosine agonists, PAF antagonists and diverse other agents. At the present time there is no consensus of the relative importance of the role played by compounds belonging to any of these general classes.

In a paper on the reactions of 2-halothiazoles with ketone enolates, J. F. Wolfe and co-workers (J. Org. Chem., 1986, 51, 1184–1188) describe bis(2-thiazolyl) derivatives of the following formula:

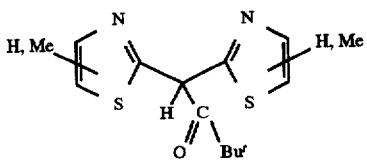

In a paper on the synthesis of 2-aroyloxazoles (Synthesis, 1984, 1048–1050), the following compound is disclosed:

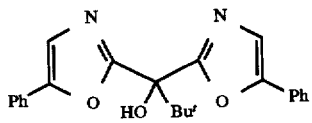

No pharmacological activity is associated with any of the above compounds. The substitution pattern of the above compounds places them outside the scope of the present invention.

In patent application DE 2801794 (US 4371734) a process for the preparation of thiazoles of general formula:

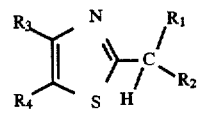

is claimed. A specific example of said thiazoles is 4-methyl-α-(4-phenyl-2-thiazolyl)-2-thiazoleacetonitrile. Said compounds are useful as intermediates in the preparation of certain dyestuffs. No pharmacological action is ascribed to said compounds. The definition of the groups $R_1$ and $R_2$ places these compounds outside the scope of the present invention.

In a paper on the synthesis of deuterium—labelled thiazoles, Roussel and Metzger (Bull. Soc. Chim. Fr., 1962, 2075–2078) describe the isolation and partial characterisation of 1,1-di(2-thiazolyl)ethanol. No pharmacological activity is associated with this compound. This compound is deleted from the scope of the present invention by a disclaimer in claim 1.

The present invention

A primary objective of the present invention is to provide structurally novel heterocyclic compounds which by virtue of their pharmacological profile are expected to be of value in the treatment of acute and chronic neuropsychiatric disorders characterised by progressive processes that sooner or later lead to neuronal cell death and dysfunction. Such disorders include stroke; cerebral ischaemia; dysfunctions resulting from brain and/or spinal trauma; hypoxia and anoxia, such as from drowning, and including perinatal and neonatal hypoxic asphyxial brain damage; multi-infarct dementia; AIDS dementia; neurodegenerative diseases such as Alzheimer's disease, Parkinson's disease, Huntington's chorea, epilepsy, multiple sclerosis and amytrophic lateral sclerosis; brain dysfunction in connection with surgery involving extracorporeal circulation or in connection with brain surgery, including endarterectomy of the carotid arteries; and CNS dysfunctions as a result of exposure to neurotoxins or radiation. This utility is manifested, for example, by the ability of these compounds to inhibit delayed neuronal death in the gerbil bilateral occlusion model of ischaemia.

The present invention relates to a compound having the general formula (1)

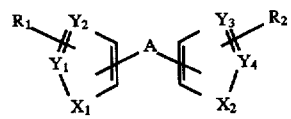

wherein:

$X_1$ and $X_2$ are independently O, S or Se;

$Y_1$ and $Y_2$ are independently C or N with the proviso that at least one of $Y_1$ and $Y_2$ is N;

$Y_3$ and $Y_4$ are independently C or N with the proviso that at least one of $Y_3$ and $Y_4$ is N;

$R_1$ and $R_2$ each represent one or more groups independently selected from H, lower alkyl, lower alkoxy-lower alkyl, hydroxy-lower alkyl, lower acyloxy-lower alkyl or $CF_3$;

and A is

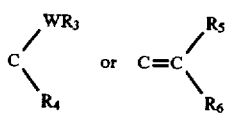

wherein

W is O, S, NH or N-lower alkyl,

R$_3$ is H, lower alkyl or lower acyl, or WR$_3$ is H,

R$_4$ is lower alkyl or lower perfluoroalkyl, or R$_3$ and R$_4$ together form a ring

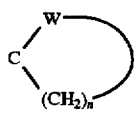

wherein n is 2, 3 or 4,

R$_5$ and R$_6$ independently are H or lower alkyl;

geometrical and optical isomers and racemates thereof where such isomers exist, as well as pharmaceutically acceptable acid addition salts thereof and solvates thereof;

with the proviso that 1,1-di(2-thiazolyl)ethanol is excluded.

The expression "pharmaceutically acceptable acid addition salts" is intended to include but is not limited to such salts as the hydrochloride, hydrobromide, hydroiodide, nitrate, hydrogen sulphate, dihydrogen phosphate, ethanedisulphonate, mesylate, fumarate, maleate and succinate.

Preferred embodiments of this invention relate to compounds having the general formula (2)

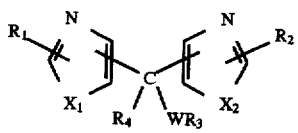

wherein:

X$_1$ and X$_2$ are independently O or S; and W, R$_1$, R$_2$, R$_3$ and R$_4$ are as previously defined above.

More preferred embodiments of this invention relate to compounds having the general formula (3)

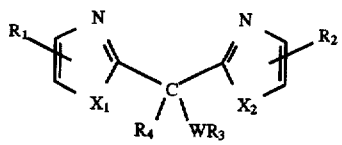

wherein:

X$_1$ and X$_2$ are independently O or S;

W is O, NH or N-lower alkyl;

and R$_1$, R$_2$, R$_3$ and R$_4$ are as previously defined above.

Analogous compounds wherein X$_1$ and/or X$_2$ are Se, for example, 1,1-bis(2-selenazolyl)-2,2,2-trifluoroethanol and 1,1-bis(2-selenazolyl)ethylamine are specifically included within the scope of the invention.

Throughout the specification and the appended claims, a given chemical formula or name shall encompass all geometrical and optical isomers and racemates thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term "lower alkyl" denotes a straight or branched alkyl group having from 1 to 6 carbon atoms. Examples of said lower alkyl include methyl, ethyl, n-propyl, isopropyl, n-butyl, isobutyl, t-butyl and straight- and branched-chain pentyl and hexyl.

Unless otherwise stated or indicated, the term "lower perfluoroalkyl" denotes a straight or branched alkyl group having from 1 to 4 carbon atoms fully substituted by fluorine. Examples of said lower perfluoroalkyl groups include trifluoromethyl, pentafluoroethyl and heptafluoroisopropyl.

Unless otherwise stated or indicated, the term "lower acyl" denotes a straight or branched acyl group having from 1 to 6 carbon atoms. Examples of said lower acyl include formyl, acetyl, propionyl, iso-butyryl, valeryl, and pivaloyl.

Unless otherwise stated or indicated, the term "hydroxy-lower alkyl" denotes a lower alkyl group as defined above substituted by a hydroxy group. Examples of said hydroxy-lower alkyl include hydroxymethyl, 1-hydroxyethyl and 2-hydroxyethyl.

Unless otherwise stated or indicated, the term "lower acyloxy-lower alkyl" denotes a lower alkyl group as defined above substituted by an oxygen atom which itself bears a lower acyl group as defined above. Examples of said lower acyloxy-lower alkyl include acetoxymethyl, propionyloxymethyl, 1-acetoxyethyl and 2-acetoxyethyl.

Unless otherwise stated or indicated, the term "lower alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term "lower alkoxy-lower alkyl" denotes a lower alkyl group as defined above substituted by a lower alkoxy group as defined above. Examples of said lower alkoxy-lower alkyl include methoxymethyl, ethoxymethyl, methoxyethyl and ethoxyethyl.

Among the most preferred compounds of formula (1) according to the present invention are:

1,1-bis(4,5-dimethyl-2-thiazolyl)ethanol;

1,1-di(2-thiazolyl)-2,2,2-trifluoroethanol;

and pharmaceutically acceptable acid addition salts or solvates thereof.

The present invention also relates to processes for preparing the compound having formula (1). Throughout the following general description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups are described, for example, in "Protective Groups in Organic Synthesis", T. W. Greene, Wiley-Interscience, New York, 1981.

Said compound wherein A is

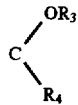

may be prepared by (a) reacting a compound of general formula (4) with an organometallic derivative of general formula (5)

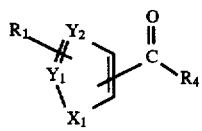 (4)

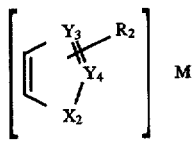 (5)

or (b) reacting a compound of general formula (6) with an organometallic derivative of general formula (7)

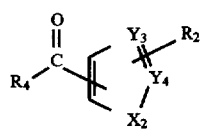 (6)

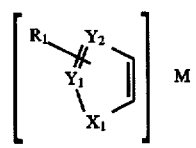 (7)

or (c) reacting a compound of general formula (8) with an organometallic derivative of general formula R$_4$M

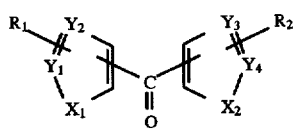 (8)

and quenching the reaction mixture with a proton source (R$_3$ is H) or an alkylating (R$_3$ is lower alkyl) or acylating (R$_3$ is lower acyl) reagent, or (d), particularly in cases where R$_4$ is perfluoroalkyl, reacting a compound of general formula (8) with a silyl derivative of general formula R$_4$SiMe$_3$.

Alternatively, the compound of formula (1) wherein A is

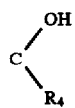

may be first obtained as above and then converted into the compound wherein R$_3$ is lower alkyl or lower acyl.

The processes (a), (b) or (c) can be achieved for example, by reacting together a ketone of structure (4) or (6) or (8) with a preformed organometallic derivative (5) or (7) or R$_4$M respectively in a suitable anhydrous solvent such as diethylether, tetrahydrofuran or hexane or mixtures thereof. Said reaction should be conducted at a suitable temperature, normally between −100° C. and +50° C. and preferably under an inert atmosphere, normally nitrogen or argon. In a specific variation, a solution of the ketone of structure (4) or (6) or (8) in anhydrous diethylether or tetrahydrofuran is added dropwise to the organometallic derivative (5) or (7) or R$_4$M respectively in anhydrous diethylether or tetrahydrofuran or hexane or mixtures thereof at a temperature of about −50° C. to −78° C. and under an atmosphere of nitrogen. After a suitable period of time the reaction mixture is allowed to warm to room temperature and then quenched by the addition of water or a lower alcohol. The required product (1) wherein A is

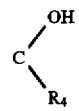

may then be isolated and purified and characterised using standard techniques.

The process (d) can be achieved, for example, by treating a solution of the ketone (8) and the silyl derivative R$_4$SiMe$_3$ in a suitable anhydrous solvent such as diethylether or tetrahydrofuran with tetrabutylammonium fluoride. Said reaction should be conducted at a suitable temperature, normally between −100° C. and +50° C. and preferably under an inert atmosphere, normally nitrogen or argon. After a suitable period of time the reaction mixture is allowed to come to room temperature and is then treated with 6M hydrochloric acid. The required product (1) wherein A is

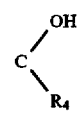

may then be isolated and purified and characterised using standard techniques.

Ketones of general formula (4) or (6) or (8) are either compounds which are commercially available or have been previously described in the literature, or compounds which can be prepared by the straightforward application of known methods.

Thus, the present invention also refers to some new intermediates of general formula (9), namely:

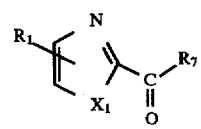 (9)

wherein:

R$_1$ and R$_2$ are as defined above;

R$_7$ is perfluoroalkyl or

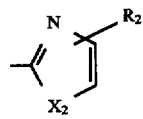

and X$_1$ and X$_2$ are independently O, S or Se; with the proviso that di(2-thiazolyl) ketone is excluded.

In the organometallic derivatives of general formula (5) or (7) or R$_4$M, M represents a metallic residue such as Li or Mg-halogen. Such compounds are either commercially available or have been previously described in the literature, or can be prepared by the straightforward application of known methods of organometallic chemistry.

Silyl derivatives of formula R$_4$SiMe$_3$ are either commercially available, for example, CF$_3$SiMe$_3$, or have been previously described in the literature or can be prepared by the straightforward application of known methods.

Compounds of formula (1) wherein A is

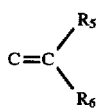

may be prepared by (a) elimination of HWR$_3$ from a compound of formula (1) wherein A is

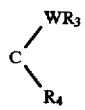

or (b) by using a compound of general formula (8) as the substrate for a standard alkene forming reaction such as the Wittig reaction, the Peterson reaction or the McMurry reaction.

The process (a) can be achieved, for example, by treatment of a solution of a compound of formula (1) wherein A is

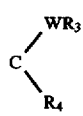

in a suitable inert solvent with an acid or a base or a reagent such as thionyl chloride or phosphorus oxychloride. Said reaction should be conducted at a suitable temperature, normally between −20° C. and the reflux temperature of the solvent. In a preferred variation, a solution of a compound of formula (1) wherein A is

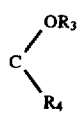

in a solvent such as dichloromethane or chloroform at 0° C. to 10° C. is treated with an acid such as anhydrous hydrogen chloride or p-toluenesulphonic acid, or with thionyl chloride. The reaction is then allowed to proceed at ambient temperature or above. The required product (1) wherein A is

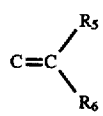

may then be isolated and purified and characterised using standard techniques.

Compounds of formula (1) wherein A is

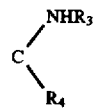

may be prepared by (a) using a compound of general formula (1) wherein A is

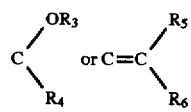

as the substrate for a Ritter reaction, or (b) by using a compound of general formula (1) wherein A is

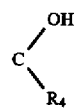

as the substrate for a Mitsunobu-type reaction, or (c) reacting a compound of general formula (1) wherein A is

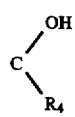

with trimethylsilylazide, Me$_3$SiN$_3$, in the presence of a Lewis acid such as boron trifluoride diethyletherate to give an azide of formula (1) wherein A is

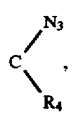

and then reducing said azide using, for example, hydrogen in the presence of a palladium or platinium catalyst.

Some compounds of general formula (1) contain an asymmetric centre and can thus exist in enantiomeric forms. These enantiomers may be separated using methods that will be well known to one skilled in the art. Such methods include, for example, (i) direct separation by means of chiral chromatography, for example, by HPLC using a chiral column;

or (ii) recrystallisation of the diastereomeric salts formed by reacting the base (1) with an optically active acid;

or (iii) derivatization of the compound of formula (1) by reaction with an optically active reagent, separation of the resultant diastereoisomeric derivatives by, for example, crystallisation or chromatography, followed by regeneration of the compound of formula (1).

Alternatively, compounds of formula (1) may be obtained directly in an optically active form by using a chemical or enzymatic based method of asymmetric synthesis.

Some compounds of general formula (1) wherein A is

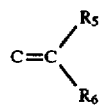

can exist as E and Z (trans and cis) isomers. Such isomers may be separated using standard techniques, for example, crystallisation or chromatography, that will be readily apparent to one skilled in the art.

Pharmacology

The neuroprotective properties of the compounds of formula (1) are exemplified by their ability to inhibit delayed neuronal death in the gerbil bilateral occlusion model of ischaemia.

Animals used were male Mongolian gerbils (60–80 g). Drugs were dissolved in isotonic saline containing dimethylsulphoxide.

Ischaemia was induced in the gerbils by 5 minute occlusion of both carotid arteries following the procedure described by R. Gill, A. C. Foster and G. N. Woodruff, J. Neuroscience. 1987, 7, 3343–3349. Body temperature was maintained at 37° C. throughout. Restoration of blood flow after occlusion was checked visually and the animals were allowed to survive for 4 days. The extent of neuronal degeneration in the hippocampus was then assessed. The test compounds were administered (i.p.) as a single dose 60 minutes following occlusion. No administration was made prior to the occlusion. The effectiveness of the compounds of formula (1) in decreasing damage to the CA1/CA2 hippocampal neurones in gerbils following ischaemic insult clearly illustrates the usefulness of these compounds in preventing neurodegeneration. These compounds are therefore expected to be of value in the treatment of acute and chronic neuropsychiatric disorders characterised by progressive processes that sooner or later lead to neuronal cell death and dysfunction.

Pharmaceutical Formulations

The administration in the novel method of treatment of this invention may conveniently be oral, rectal, topical or parenteral at a dosage level of, for example, about 0.01 to 1000 mg/kg, preferably about 1.0 to 500 mg/kg and especially about 5.0 to 200 mg/kg and may be administered on a regimen of 1 to 4 doses or treatments per day. The dose will depend on the route of administration, preferred routes being oral or intravenous administration. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; suppositories for rectal administration; or suitable topical formulations. Conventional procedures for the selection and preparation of suitable pharmaceutical formulations are described, for example, in "Pharmaceuticals—The Science of Dosage Form Design", M. E. Aulton, Churchill Livingstone, 1988.

To produce pharmaceutical formulations containing a compound according to the present invention in the form of dosage units for oral application the active substance may be admixed with an adjuvant/a carrier e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.02% to about 20% by weight of the active substance herein described, the balance being sugar and a mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may involve the use of surface acting agents to improve solubility. They may conveniently be provided in various dosage unit ampoules.

Except where otherwise indicated, the necessary starting materials for all Preparations and Examples were purchased commercially.

PREPARATION 1

4-Methyl -2-trifluoroacetylthiazole n-Butyllithium (2.5M solution in hexanes, 40.4 ml) was added dropwise to a stirred solution of 4-methylthiazole (10 g) in anhydrous tetrahydrofuran at −70° C. under an atmosphere of dry nitrogen. After 30 minutes, ethyl trifluoroacetate (12 ml) was added dropwise. After a further 2 hours the mixture was allowed to warm to room temperature and was then left stirring overnight. Saturated aqueous ammonium chloride solution was added and the organic phase was separated, dried and evaporated to dryness. The residue was purified by flash chromatography to give the hydrate corresponding to the title compound as a white solid.

M.p. 77°–81° C.

$^{13}$C Nmr ($d_6$-DMSO) 16.4, 91.1 (q J 32 Hz), 116.3, 122.2 (q, J 287 Hz), 152.0 and 166.6 ppm.

Found: C, 33.8; H, 2.7; N, 6.6. $C_6H_6F_3NO_2S$ requires C, 33.8; H, 2.8; N, 6.6%.

Following the general method of Preparation 1 and using the appropriate thiazole the compounds of Preparations 2 and 3 were prepared.

PREPARATION 2

4,5-Dimethyl-2-trifluoroacetylthiazole (as the corresponding hydrate)

M.p. 84°–86° C.

Found: C, 37.15; H, 3.4; N, 5.9. $_7H_8F_3NO_2S$ requires C, 37.0; H, 3.55; N, 6.2%

PREPARATION 3

2-Trifluoroacetylthiazole (as the corresponding hydrate)

M.p. 80°–82° C.

$^{13}$C Nmr ($d_6$-DMSO) 91.7 (q, J 32 Hz), 122.4, 122.7 (q, J 287 Hz), 142.9 and 167.9 ppm.

PREPARATION 4

2-Acetyl-5-(2-methoxyethyl)-4-methylthiazole

From 5-(2-methoxyethyl)-4-methylthiazole and ethyl acetate, following the procedure of Preparation 1.

$^{13}$C Nmr (CDCl$_3$) 15.1, 25.6, 27.6, 58.7, 71.9, 137.9, 151.6, 163.0 and 191.5 ppm.

PREPARATION 5

5-(2-Methoxyethyl)-4-methyl-2-trifluoroacetylthiazole

From 5-(2-methoxyethyl)-4-methylthiazole and ethyl trifluoroacetate, following the procedure of Preparation 1.

$^{13}$C Nmr (CDCl$_3$) 15.2, 27.8, 58.6, 71.3, 116.2 (q, J 288 Hz), 142.2, 154.1, 155.8 and 173.0 (q, J 36 Hz) ppm.

PREPARATION 6

4-Methyl-2-trifluoroacetyloxazole

1-Trifluoroacetylimidazole (10 g) was added to a stirred solution of 4-methyl-2-trimethylsilyloxazole (J. Chem. Soc., Chem. Commun., 1984, 258) (9.95 g) in diethyl ether (100 ml) at 0° C. After 20 hours, water was added. The organic phase was separated, dried and evaporated and the residue was purified by flash chromatography to give the title compound as the corresponding hydrate.

$^{13}$C Nmr (d$_6$-DMSO) 11.0, 89.5, (q, J 33 Hz), 122.3 (q, J 287 Hz), 136.0, 136.1 and 158.6 ppm.

PREPARATION 7

Bis(4-methyl-5-thiazolyl) Ketone n-Butyllithium (2.5M solution in hexanes, 12.8 ml) was added dropwise to a stirred solution of 4-methyl-2-trimethylsilylthiazole (5 g) in anhydrous tetrahydrofuran/diethyl ether/pentane (4:4:1, 75 ml) at −100° C. under an atmosphere of dry nitrogen. After 90 minutes, 4-methyl-5-thiazolecarbaldehyde (J. Amer. Chem. Soc., 1982, 104, 4934–4943) (4 g) was added. After a further 3 hours at −100° C., water was added and the mixture was warmed to room temperature. Saturated aqueous ammonium chloride solution was added and the organic phase was separated, dried and evaporated. The residue was crystallised from ethyl acetate to give bis(4-methyl-5-thiazolyl)methanol. This material in dichloromethane was oxidised using manganese dioxide to give the title compound.

$^1$H Nmr (CDCl$_3$) 2.73 (6H, s) and 8.85 (2H, s) ppm.

PREPARATION 8

Bis(4-methyl-2-oxazolyl) Ketone

Triphosgene (2.9 g) in anhydrous dichloromethane (25 ml) was added dropwise to a stirred solution of 4-methyl-2-trimethylsilyloxazole (10 g) in dichloromethane (50 ml) at 0° C. The mixture was then stirred overnight at ambient temperature. Saturated aqueous ammonium chloride solution was added. The organic phase was separated, washed, dried and evaporated. Purification by flash chromatography then gave the title compound.

$^{13}$C Nmr (CDCl$_3$) 11.7, 138.7, 140.2, 155.9 and 164.6 ppm.

EXAMPLE 1

1,1-Bis(4-methyl-2-thiazolyl)ethanol n-Butyllithium (2.5M solution in hexanes, 44.4 ml) was added dropwise to a stirred solution of 4-methylthiazole in anhydrous tetrahydrofuran (100 ml) at −70° C. under an atmosphere of dry nitrogen. After 30 minutes, ethyl acetate (4 g) in tetrahydrofuran (25 ml) was added dropwise. After a further 1 hour, the mixture was allowed to warm to room temperature and was then left to stir overnight. Saturated aqueous sodium hydrogen carbonate solution was added and the organic phase was separated. Further processing in the usual fashion and crystallisation from diethyl ether then gave the title compound.

M.p. 82°–84° C.

$^{13}$C Nmr (CDCl$_3$) 17.0, 31.2, 76.1, 114.7, 152.2 and 174.4 ppm.

Treatment with anhydrous hydrogen chloride in diethyl ether gave the corresponding hydrochloride.

M.p. 135° C. (dec.).

$^{13}$C Nmr (d$_6$-DMSO) 16.3, 28.9, 75.2, 115.6, 150.8 and 175.5 ppm.

Following the general method of Example 1 and using the appropriate thiazole with the appropriate ester, the compounds of Examples 2 to 5 were prepared.

EXAMPLE 2

1,1-Bis (4,5-dimethyl-2-thiazolyl)ethanol

M.p. 143°–144° C.

$^{13}$C Nmr (CDCl$_3$) 11.2, 14.6, 30.8, 75.8, 127.5, 147.3 and 170.3 ppm.

Found: C, 53.7; H, 5.95; N, 10.3. C$_{12}$H$_{16}$N$_2$OS$_2$ requires C, 53.7; H, 6.0; N, 10.44%

Hydrochloride, m.p. 146°–147° C. Found: C, 47.2; H, 5.7; N, 9.0. C$_{12}$H$_{16}$N$_2$OS$_2$. HCl requires C, 47.3; H, 5.6; N, 9.2%.

EXAMPLE 3

1,1-Bis(4,5-dimethyl-2-thiazolyl)-2,2-dimethyl-1-propanol

M.p. 91°–92° C.

$^{13}$C Nmr (CDCl$_3$) 11.6, 15.1, 26.0, 40.5, 83.1, 127.7, 146.8 and 168.4 ppm.

Hydrochloride, m.p. 160°–162° C. Found: C, 51.8; H, 6.7; N, 7.9. C$_{15}$H$_{22}$N$_2$OS$_2$.HCl requires C, 52.0; H, 6.7; N, 8.1%.

EXAMPLE 4

1-Bis(4,5-dimethyl-2-thiazolyl)-2-methyl-1-propanol

M.p. 106°–108° C.

$^{13}$C Nmr (CDCl$_3$) 11.2, 14.6, 16.5, 40.0, 81.0, 127.2, 146.8 and 170.1 ppm.

Hydrochloride, m.p. 169°–171° C. Found: C, 50.5; H, 6.4; N, 8.4. C$_{14}$H$_{20}$N$_2$OS$_2$.HCl requires C, 50.5; H, 6.4; N, 8.4%.

EXAMPLE 5

1,1-Bis(4-methyl-2-thiazolyl)-2,2-dimethyl-1-propanol Hydrochloride

M.p. 190°–193° C. (dec.).

$^{13}$C Nmr (d$_6$-DMSO) 16.5, 25.4, 40.0, 82.3, 115.6, 150.2 and 172.5 ppm. Found: C, 49.0; H, 6.1; N, 8.65. C$_{13}$H$_{18}$N$_2$OS$_2$.HCl requires C, 49.0; H, 6.0; N, 8.8%.

EXAMPLE 6

1,1-Di(2-thiazolyl)ethanol n-Butyllithium (2.5M solution in hexanes, 17.3 ml) was added dropwise to a stirred solution of 2-bromothiazole (6.5 g) in anhydrous diethyl ether (40 ml) at −70° C. under an atmosphere of dry nitrogen. After 30 minutes, 2-acetylthiazole (5 g) in diethyl ether (10 ml) was added dropwise. After a further 1 hour, the mixture was allowed to warm to room temperature. After 1 hour, saturated aqueous sodium hydrogen carbonate solution was added and the organic phase was separated. Further processing in the usual fashion then gave the title compound.

M.p. 146°–147° C.

$^{13}$C Nmr (CDCl$_3$) 31.4, 76.4, 120.3, 142.0 and 175.2 ppm.

Found: C, 45.1; H, 3.5; N, 13.0. C$_8$H$_8$N$_2$OS$_2$ requires C, 45.2; H, 3.8; N, 13.2%.

Hydrochloride, m.p. 137°–140° C. (dec.).

$^{13}$C Nmr (d$_6$-DMSO) 28.8, 75.4, 129.6, 142.0 and 176.0 ppm.

Following the general method of Example 6 the compounds of Examples 7 to 13 were prepared.

EXAMPLE 7

1-(4-Methyl-2-oxazolyl)-1-(2-thiazolyl)ethanol

From 2-bromothiazole and 2-acetyl-4-methyloxazole (J. Chem. Soc., Chem. Commun., 1984, 258).

$^{13}$C Nmr (CDCl$_3$) 11.3, 27.9, 73.1, 119.9, 135.4, 136.4, 142.6, 164.6 and 174.1 ppm.

EXAMPLE 8

1,1-Di(2-thiazolyl)-2,2,2-trifluoroethanol

From 2-bromothiazole and 2-trifluoroacetylthiazole.

M.p. 113°–115° C.

$^{13}$C Nmr (d$_6$-DMSO) 77.3 (q, J 30 Hz), 122.8, 123.0 (q, J 286 Hz), 142.7 and 166.1 ppm.

Found: C, 36.25; H, 1.7; N, 10.5. C$_8$H$_5$F$_3$N$_2$OS$_2$ requires C, 36.1; H, 1.9; N, 10.5%.

EXAMPLE 9

1,1-Bis(4,5-dimethyl-2-thiazolyl)-2,2,2-trifluoroethanol

From 4,5-dimethylthiazole and 4,5-dimethyl-2-trifluoroacetylthiazole.

M.p. 122°–123.5° C.

$^{13}$C Nmr (d$_6$-DMSO) 10.5, 14.4, 76.9 (q, J 30 Hz) 123.1 (q, J 286 Hz), 129.0, 147.9 and 161.0 ppm.

EXAMPLE 10

1,1-Bis(4-methyl-2-thiazolyl)-2,2,2-trifluoroethanol

From 4-methylthiazole and 4-methyl-2-trifluoroacetylthiazole and using anhydrous tetrahydrofuran as solvent.

M.p. 140°–142.5° C.

$^{13}$C Nmr (CDCl$_3$) 17.0, 77.5 (q, J 31 Hz), 117.1, 122.6 (q, J 284 Hz), 152.5 and 163.9 ppm.

EXAMPLE 11

1,1-Bis(5-(2-methoxyethyl)-4-methyl-2-thiazolyl)ethanol

From 5-(2-methoxyethyl)-4-methylthiazole and 2-acetyl-5-(2-methoxyethyl)-4-methylthiazole.

M.p. 50°–51° C.

13C Nmr (CDCl$_3$) 14.8, 27.0, 30.8, 58.5, 72.4, 75.8, 129.3, 147.6 and 171.3 ppm.

EXAMPLE 12

1,1-Bis(5-(2-methoxyethyl)-4-methyl-2-thiazolyl)-2,2,2-trifluoroethanol

From 5-(2-methoxyethyl)-4-methylthiazole and 5-(2-methoxyethyl)-4-methyl-2-trifluoroacetylthiazole.

M.p. 68°–69° C.

$^{13}$C Nmr (d$_6$-DMSO) 14.6, 26.0, 57.7, 71.4, 77.0 (q, J 30 Hz), 123.1 (q, J 286 Hz), 131.4, 148.1 and 162.0 ppm.

EXAMPLE 13

1-(2,4-Dimethyl-5-thiazolyl)-1-(2-thiazolyl)ethanol $^{13}$C Nmr (CDCl$_3$) 16.3, 18.7, 31.6, 73.6, 119.9, 136.4, 142.2, 148.3, 162.7 and 176.9 ppm.

EXAMPLE 14

1,1-Bis(4-methyl-5-thiazolyl)-2,2,2-trifluoroethanol (Trifluoromethyl)trimethylsilane (494 μl) was added to a stirred solution of bis(4-methyl-5-thiazolyl) ketone (500 mg) in anhydrous tetrahydrofuran (20 ml) at room temperature. After 1 hour, tetrabutylammonium fluoride (300 mg) was added. The mixture was stirred for 2 hours and then 3M hydrochloric acid was added. After 10 minutes the reaction mixture was adjusted to pH10 by the addition of 5M potassium hydroxide. The organic phase was separated and then worked-up in the usual manner to give the title compound.

$^{13}$C Nmr (d$_6$-DMSO) 15.9, 73.7 (q, J 31 Hz), 124.9 (q, J 285 Hz), 128.0, 152.1 and 152.8 ppm.

EXAMPLE 15

1,1-Bis(4-methyl-2-oxazolyl)-2,2,2-trifluoroethanol

Following the method of Example 14 and using bis(4-methyl-2-oxazolyl) ketone and dichloromethane as solvent, the title compound was prepared.

$^{13}$C Nmr (CDCl$_3$) 14.7, 76.8 (q, J 32 Hz), 125.9 (q, J 285 Hz), 140.5, 140.8 and 160.1 ppm.

EXAMPLE 16

1-(2,4-Dimethyl-5-thiazolyl)-1-(4-methyl-2-thiazolyl)ethanol n-Butyllithium (2.5M solution in hexanes, 5.1 ml) was added dropwise to a stirred solution of 4-methyl-2-trimethylsilylthiazole (from 4-methylthiazole, n-butyllithium and trimethylsilylchloride) (2 g) in anhydrous tetrahydrofuran (40 ml) at −70° C. under an atmosphere of dry nitrogen. After 30 minutes, 5-acetyl-2,4-dimethylthiazole (2 g) in tetrahydrofuran (10 ml) was added dropwise. After 1 hour the mixture was allowed to warm to room temperature. After a further 2 hours, saturated aqueous ammonium chloride solution was added. The organic phase was separated, washed, dried and evaporated. The residue was dissolved in tetrahydrofuran (2 ml) and tetrabutylammonium fluoride (640 mg) was added. The mixture was stirred overnight and then worked up in the usual fashion to give the title compound.

$^{13}$C Nmr (CDCl$_3$) 16.4, 17.0, 18.7, 31.5, 73.3, 114.4, 136.3, 148.2, 152.3, 162.6 and 175.7 ppm.

Found: C, 51.7; H, 5.4; N, 10.8. C$_{11}$H$_{14}$N$_2$OS$_2$ requires C, 51.9; H, 5.55; N, 11.0%.

EXAMPLE 17

1,1-Bis(4,5-dimethyl-2-thiazolyl)-2,2,2-trifluoroethyl Acetate

Acetyl chloride (0.68 ml) was added to a solution of 1,1-bis(4,5-dimethyl-2-thiazolyl)-2,2,2-trifluoroethanol (1.54 g) and 4-dimethylaminopyridine (2 g) in dry dichloromethane (70 ml). The mixture was stirred at room temperature overnight and was then washed with saturated aqueous sodium hydrogen carbonate solution. The organic phase was separated, dried and evaporated and the residue was purified by flash chromatography to give the title compound.

M.p. 163°–164° C.

Found: C, 45.9; H, 4.0; N, 7.4. $C_{14}H_{15}F_3N_2O_2S_2$ requires C, 46.15; H, 4.15; N, 7.7%

EXAMPLE 18

1-Di(2-thiazolyl)-2,2,2-trifluoroethyl Acetate

From 1,1-di(2-thiazolyl)-2,2,2-trifluoroethanol using the method of Example 17.

M.p. 82°–84° C.

$^{13}$C Nmr (CDCl$_3$) 21.2, 81.4 (q, J 31 Hz), 121.4 (q, J 284 Hz), 122.5, 142.2, 161.1 and 167.5 ppm.

EXAMPLE 19

1-Azido-1-(2,4-dimethyl-5-thiazolyl)-1-(2-thiazolyl)ethane 1-(2,4-Dimethyl-5-thiazolyl)-1-(2-thiazolyl)ethanol (200 mg) was suspended in benzene (2 ml) at room temperature. Diphenylphosphoryl azide (212 µl) was added, followed by 1,8-diazabicyclo[5.4.0]undec-7-ene (152 µl). The mixture was stirred at ambient temperature for 72 hours and was then diluted with ethyl acetate and water. Work-up in the usual fashion including flash chromatography then gave the title compound.

$^{13}$C Nmr (CDCl$_3$) 16.4, 18.9, 28.4, 64.9, 120.3, 132.4, 143.0, 149.4, 163.3 and 172.3 ppm.

EXAMPLE 20

1-(2,4-Dimethyl-5-thiazolyl)-1-(2-thiazolyl)ethylamine

The product from Example 19 in ethanol was hydrogenated in the presence of 10% palladium-on-charcoal to give the title compound.

$^1$H Nmr (CDCl$_3$) 2.02, 2.08 and 2.61 (each 3H, s), 2.23 (2H, br s) and 7.28 and 7.73 (each 1H, d, J 3 Hz) ppm.

EXAMPLE 21

1,1-Di(2-thiazolyl)-2,2,2-trifluoroethyl Methyl Ether 1,1-Di(2-thiazolyl)-2,2,2-trifluoroethanol (1 g) was added to a stirred suspension of sodium hydride (80%, 225 mg) in dry dimethoxyethane (50 ml) at 0° C. After 15 minutes, methyl iodide (2.1 g) was added dropwise. The mixture was allowed to warm to room temperature and was then left stirring overnight. The mixture was concentrated by evaporation, then poured into saturated aqueous sodium chloride solution and extracted with dichloromethane. The material thus obtained was purified by flash chromatography to give the title compound as a white solid (950 mg).

M.p. 40°–41° C.

$^{13}$C Nmr (CDCl$_3$) 54.9, 82.9 (q, J 30 Hz), 122.2, 122.8 (q, J 287 Hz), 143.2 and 163.6 ppm.

Found: C, 38.7; H, 2.4; N, 9.9. $C_9H_7F_3N_2OS_2$ requires C, 38.6; H, 2.5; N, 10.0%

EXAMPLE 22

1,1-Di(5-thiazolyl)-2,2,2-trifluoroethanol n-Butyllithium (2.5M solution in hexanes, 13.9 ml) was added dropwise to a stirred solution of 2-trimethylsilylthiazole (5 g) in anhydrous tetrahydrofuran/diethyl ether/pentane (4:4:1, 75 ml) at −100° C. under an atmosphere of dry nitrogen. After 1 hour, trifluoroacetic anhydride (3 g) in the above solvent mixture (15 ml) was added dropwise. After a further 3 hours at −100° C., water was added and the mixture was warmed to room temperature. Saturated aqueous ammonium chloride solution was added and the organic phase was separated, dried and evaporated. Flash chromatography followed by recrystallisation from diethyl ether gave the title compound as a white solid.

M.p. 109°–110° C.

$^{13}$C Nmr (CDCl$_3$) 74.5 (q, J 33 Hz), 123.9 (q, J 286 Hz), 138.1, 142.0 and 155.0 ppm.

Found: C, 36.1; H, 1.9; N, 10.3. $C_8H_5F_3N_2OS_2$ requires C, 36.1; H, 1.9; N, 10.5%

EXAMPLE 23

1,1-Di(4-thiazolyl)-2,2,2-trifluoroethanol n-Butyllithium (2.5M solution in hexanes, 2.5 ml) was added dropwise to a stirred solution of 4-bromo-2-trimethylsilylthiazole (Synthesis, 1986, 757) (1.5 g) in anhydrous diethyl ether (25 ml) at −78° C. under an atmosphere of dry nitrogen. After 30 minutes, trifluoroacetic anhydride (300 µl) was added dropwise. After a further 1 hour at −78° C., the mixture was warmed to room temperature. After 1 hour, hydrochloric acid (1M, 10 ml) was added and the mixture was stirred for 1 hour. The organic phase was then separated. The material thus obtained was purified by flash chromatography to give the title compound as a white solid.

M.p. 87°–89° C.

$^{13}$C Nmr (CDCl$_3$) 75.6 (q, J 31 Hz), 118.6, 123.9 (q, J 286 Hz), 152.4 and 152.6 ppm.

EXAMPLE 24

1-(4-Methyl-2-thiazolyl)-1-(2-thiazolyl)-2,2,2-trifluoroethanol

From 4-methylthiazole and 2-trifluoroacetylthiazole using the general method of Example 6.

M.p. 89°–90° C.

PHARMACY EXAMPLES

The following examples illustrate suitable pharmaceutical compositions to be used in the method of the invention.

| Composition 1 - Tablets | |
|---|---|
| Compound of Example 8 | 10 g |
| Lactose | 94 g |
| Microcrystalline cellulose | 86 g |
| Polyvinylpyrrolidone | 8 g |
| Magnesium stearate | 2 g |

The compound of Example 8, lactose, cellulose and polyvinylpyrrolidone are sieved and blended. The magnesium stearate is sieved and then blended into the above mixture. Compression using suitable punches then yields 1000 tablets each containing 10 mg of the active ingredient. If desired, the obtained tablets can then be film coated.

| Composition 2 - Tablets | |
|---|---|
| Compound of Example 8 | 50 g |
| Lactose | 80 g |
| Microcrystalline cellulose | 20 g |
| Potato starch | 40 g |
| Polyvinylpyrrolidone | 8 g |
| Magnesium stearate | 2 g |

The compound of Example 8, lactose, cellulose and part of the starch are mixed and granulated with 10% starch paste. The resulting mixture is dried and blended with the remaining starch, the polyvinylpyrrolidone and the sieved magnesium stearate. The resulting blend is then compressed to give 1000 tablets each containing 50 mg of the active ingredient.

| Composition 3 - Capsules | |
| --- | --- |
| Compound of Example 8 | 100 g |
| Pregelatinised starch | 98 g |
| Magnesium stearate | 2 g |

The compound of Example 8 and the starch are sieved, blended together and then lubricated with the sieved magnesium stearate. The blend is used to fill 1000 hard gelatine capsules of a suitable size. Each capsule contains 100 mg of the active ingredient.

| Composition 4 - Injection Formulation | |
| --- | --- |
| Compound of Example 8 | 0.5 to 10 g |
| Polyethoxylated castor oil | 15 g |
| Water for injection ad | 100 g |

Sodium chloride may be added to adjust the tonicity of the solution and the pH may be adjusted to that of maximum stability and/or facilitate solution of the compound of the invention using dilute acid or alkali or by the addition of suitable buffer salts. Antioxidants and metal chelating salts may also be included.

The solution is prepared, clarified and filled into appropriate size bottles and sealed. The formulation is sterilised by heating in an autoclave. Alternatively, the solution may be sterilised by filtration and filled into sterile bottles under aseptic conditions. The solution may be packed under a nitrogen blanket.

| Composition 5 - Injection Formulation | |
| --- | --- |
| Compound of Example 8 | 0.5 to 10 g |
| Polyethoxylated castor oil | 15 g |
| Propylene glycol | 20 g |
| Polyoxyethylene-polyoxypropylene block copolymer (Pluronic F68) | 10 g |
| Water for injection ad | 100 g |

The compound of the invention is added to a mixture of polyethoxylated castor oil, propylene glycol and Pluronic F68. The mixture is gently heated until a clear solution is obtained. This solution is sterilised by heating in an autoclave or alternatively, by the process of filtration. A concentrated sterile solution is thus obtained, which is suitable for dilution with sterile water in order to form a composition suitable for parenteral administration.

| Composition 6 - Injection Formulation | |
| --- | --- |
| Compound of Example 8 | 0.5 to 10 g |
| Hydroxypropyl-β-cyclodextrin | 10 g |
| Water for injection ad | 100 g |

Water for injection is added to a mixture of the compound of the invention and hydroxypropyl-β-cyclodextrin. The mixture is gently stirred until a clear solution is obtained. The solution is filled into bottles which are then sealed and sterilised by heating in an autoclave or alternatively, by the process of filtration.

We claim:

1. A method for the treatment of acute and chronic neuropsychiatric disorders characterized by progressive processes that lead to neuronal cell death and dysfunction which comprises administering to a host in need of such treatment a therapeutically effective amount of a compound having the general formula (1)

$$R_1 \diagdown \overset{Y_2}{\underset{Y_1}{\diagup}} \diagdown \overset{}{\underset{X_1}{\diagup}} A \overset{}{\underset{X_2}{\diagdown}} \overset{Y_3}{\underset{Y_4}{\diagup}} \diagdown R_2 \quad (1)$$

wherein:

$X_1$ and $X_2$ are independently O, S or Se;

$Y_1$ and $Y_2$ are independently C or N with the proviso that at least one of $Y_1$ and $Y_2$ is N;

$Y_3$ and $Y_4$ are independently C or N with the proviso that at least one of $Y_3$ and $Y_4$ is N;

$R_1$ and $R_2$ each represent at least on group independently selected from the group consisting of H, lower alkyl, lower alkoxy-lower alkyl, hydroxy-lower alkyl, lower acyloxy-lower alkyl and $CF_3$;

and A is $$C\diagdown\overset{WR_3}{\underset{R_4}{\diagup}} \quad \text{or} \quad C=C\diagdown\overset{R_5}{\underset{R_6}{\diagup}}$$

wherein W is O, S, NH or N-lower alkyl, $R_3$ is H, lower alkyl or lower acyl, or $WR_3$ is H, $R_4$ is lower alkyl or lower perfluoroalkyl, or $R_3$ and $R_4$ together form a ring $$\overset{W}{\underset{(CH_2)_n}{\diagup}}C$$

wherein n is 2, 3 or 4, $R_5$ and $R_6$ independently are H or lower alkyl;

geometrical and optical isomers and racemates thereof where such isomers exist, as well as pharmaceutically acceptable acid addition salts thereof and solvates thereof.

2. A method for the treatment of acute and chronic neuropsychiatric disorders characterized by progressive processes leading to neuronal cell death and dysfunction, which comprises administering to a host in need of such treatment a therapeutically effective amount of a compound having the general formula (2)

$$R_1\diagdown\overset{N}{\underset{X_1}{\diagup}}\diagdown\overset{}{\underset{R_4}{\diagup}}C\overset{}{\underset{WR_3}{\diagdown}}\overset{N}{\underset{X_2}{\diagup}}\diagdown R_2 \quad (2)$$

wherein $X_1$ and $X_2$ are independently O or S; and W is O, S, NH or N-lower alkyl, $R_1$ and $R_2$ each represent at least one group independently selected from the group consisting of H, lower alkyl, lower alkoxy-lower alkyl, hydroxy-lower alkyl, lower acyloxy-lower alkyl and $CF_3$;

$R_3$ is H, lower alkyl or lower acyl, or WR₃ is H, and

R₄ is lower alkyl or lower perfluoro-alkyl, or R₃ and R₄ together form a ring

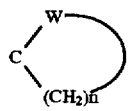

wherein n is 2, 3 or 4.

3. A method for the treatment of acute and chronic neuropsychiatric disorders characterized by progressive processes leading to neuronal cell death and dysfunction which comprises administering to a host in need of such treatment a therapeutically effective amount of a compound having the general formula (3)

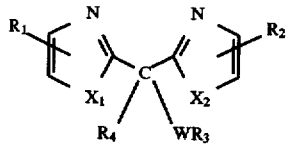

wherein $X_1$ and $X_2$ or independently O or S; W is O, NH or N-lower alkyl; and $R_1$ and $R_2$ each represent at least one group independently selected from the group consisting of H, lower alkyl, lower alkoxy-lower alkyl, hydroxy-lower alkyl, lower acyloxy-lower alkyl and $CF_3$;

$R_3$ is H, lower alkyl or lower acyl, or $WR_3$ is H, and $R_4$ is lower alkyl or lower perfluoro-alkyl, or $R_3$ and $R_4$ together form a ring

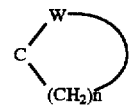

wherein n is 2, 3 or 4.

4. The method according to any one of the claims 1–3, wherein the compound is in a mixture with a pharmaceutically acceptable carrier.

5. The method according to any one of the claims 1–3, wherein the therapeutic amount ranges from about 0.01 to 1000 mg/kg for a regimen of 1 to 4 doses or treatments per day.

6. The method according to an any one of the claims 1–3, wherein the therapeutic amount ranges from about 5.0 to 200 mg/kg for a regimen of 1 to 4 doses or treatments per day.

* * * * *